United States Patent [19]

Stengel

[11] Patent Number: 5,777,748
[45] Date of Patent: Jul. 7, 1998

[54] DEVICE FOR DETERMINING DENSITY AND CONCENTRATION OF VISIBLE CONSTITUENTS IN FLUIDS

[75] Inventor: Karl Stengel, Deizisau, Germany

[73] Assignee: Robert Bosch GmbH, Stuttgart, Germany

[21] Appl. No.: 647,933

[22] PCT Filed: Dec. 3, 1994

[86] PCT No.: PCT/DE94/01443

§ 371 Date: May 29, 1996

§ 102(e) Date: May 29, 1996

[87] PCT Pub. No.: WO95/17664

PCT Pub. Date: Jun. 29, 1995

[30] Foreign Application Priority Data

Dec. 22, 1993 [DE] Germany .................. 43 43 897.0

[51] Int. Cl.$^6$ .................................................. G01N 21/00
[52] U.S. Cl. ...................................... 356/438; 250/574
[58] Field of Search .......................... 356/437, 438, 356/439, 445, 339, 441–442; 250/573–574

[56] References Cited

U.S. PATENT DOCUMENTS 2,873,644  2/1959  Kremen et al. .......................... 250/574
3,510,666  5/1970  Topol .................................... 356/441

FOREIGN PATENT DOCUMENTS 2252621  8/1992  United Kingdom.

OTHER PUBLICATIONS

R. Lenk et al.: "Fachlexikon ABC Physik". Verlag Harri Deutsch, Zuerich and Frankfurt, 1974, p. 1599.

*Primary Examiner*—K. Hantis
*Attorney, Agent, or Firm*—Spencer & Frank

[57] ABSTRACT

An arrangement is proposed for determining the density and concentration of visible constituents in fluids, particularly for measuring the turbidity of motor vehicle exhaust gases. A measuring chamber (10) which can receive the fluid to be measured is provided at two oppositely disposed points a first light detector (16) and a light source (15) which directs a light beam at the light detector (16). This arrangement allows the opacimetric measuring method in which the light attenuation is evaluated as a function of the turbidity. In addition, a second light detector (19) is arranged outside of and lateral to the radiation path through the measuring chamber (10) for capturing scattered light. This allows use of the scattered light method in which the scattered light portion is captured as a measure for the concentration of the light-scattering particles in the investigated medium. In an evaluation arrangement, the measuring signals (turbidity and scattered light) can be evaluated simultaneously or selectively.

15 Claims, 1 Drawing Sheet

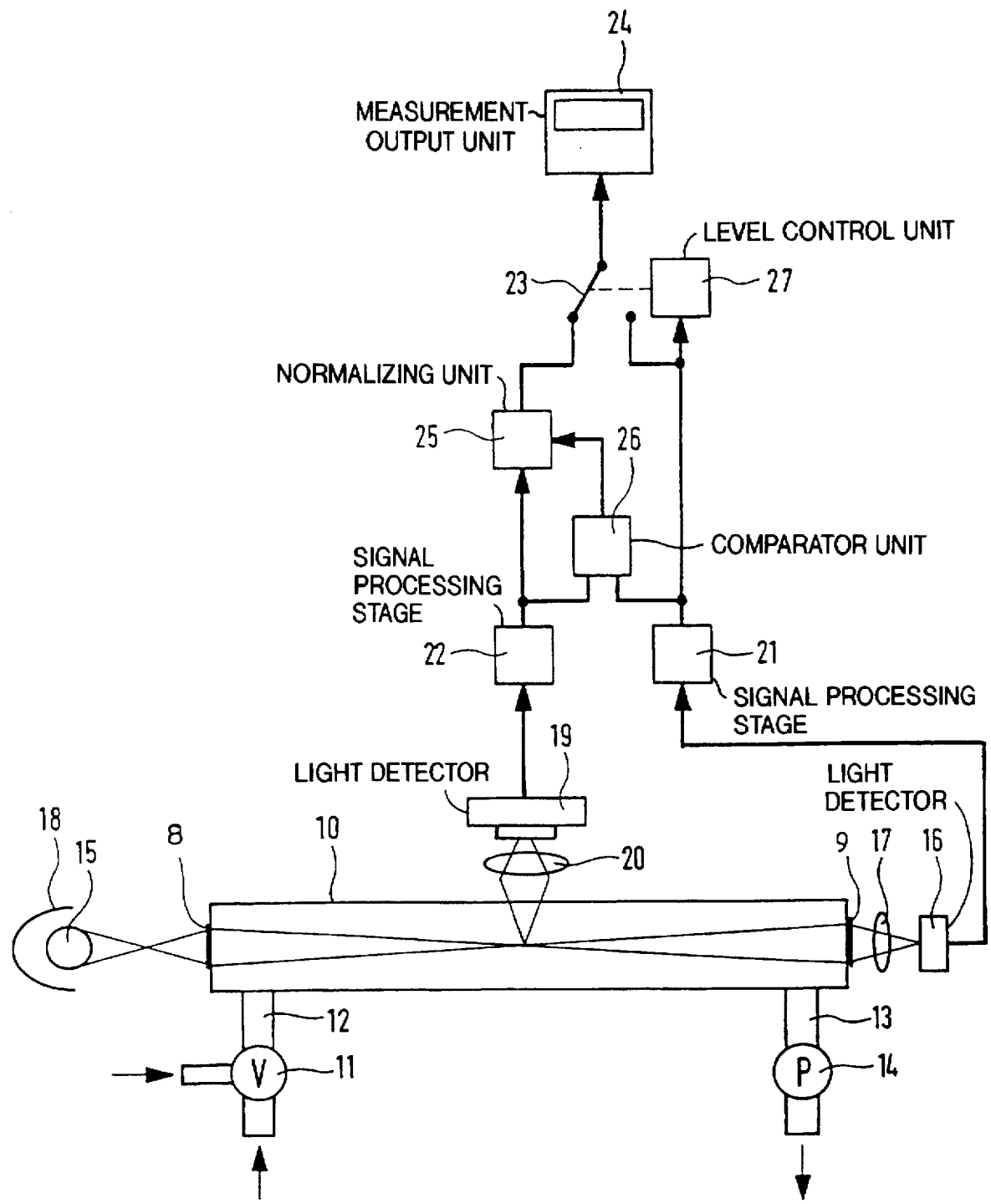

DEVICE FOR DETERMINING DENSITY AND CONCENTRATION OF VISIBLE CONSTITUENTS IN FLUIDS

BACKGROUND OF THE INVENTION

The invention relates to an arrangement for determining the density and concentration of visible constituents in fluids, particularly for measuring the turbidity of motor vehicle exhaust gases. More particularly, the invention relates to a density determining arrangement of the type having a measuring chamber through which the exhaust gas flows, which measuring chamber is provided at two oppositely disposed points with a first light detector and a light source, and having an evaluation arrangement which evaluates the signal generated by the light detector as a measure of density and concentration.

Such a turbidity measuring device or opacimeter measures the attenuation of a light beam through a measuring chamber which is filled with the fluid to be measured or through which the fluid flows, with the light attenuation taken as the measure for the turbidity. The evaluation takes place according to the Lambert-Beer law which describes the light attenuation during passage through absorbing media. The assignee of this application distributes such a turbidity measuring device under the designation RTT 100/100 which serves to measure flue gas or soot in motor vehicle exhaust gases. The drawback of the known arrangements is that this turbidity measuring method fails for exhaust gases with low soot concentrations, as they are encountered with ever increasing frequency in engines or combustion systems of a more recent design. By means of structural or combustion engineering measures, the soot emission is reduced to such an extent that the accuracy of the opacimetric measuring methods is no longer sufficient. The reason for the limited accuracy for low soot concentrations lies in the principle of the measuring method, which is based on measuring a difference between a brightness signal and an attenuated signal, i.e., a difference between two signals which are almost identical in size.

From GB 22 52 621, a scattered light measuring method is known, wherein first a light beam is also guided into a fluid to be measured. The light portion which is scattered in different directions is captured and evaluated. In scattered light methods, a measuring signal is obtained which is proportional to the concentration of the absorbing medium. This scattered light method is suited particularly for low soot concentrations, but it is inferior to the opacimetric measuring method in the range of higher concentrations.

SUMMARY OF THE INVENTION

Advantages of the Invention

The arrangement according to the invention is characterized in that a second light detector is arranged outside lateral to the radiation path through the measuring chamber for capturing scattered light, and in that the evaluation arrangement evaluates the signal generated by the second light detector independently of the signal generated by the first light detector also as a measure for the density and concentration. Such an arrangement has the advantage that the advantages of the two known measuring methods are combined with one another, with a single measuring chamber being required and with it being possible to carry out the measurements of both methods simultaneously. In this manner, considerably greater accuracy is obtained over the entire range with a measuring complexity that is hardly any more extensive, and very high and very low concentrations can be measured with great accuracy.

Advisably, the measuring chamber is configured as a measuring tube through which the fluid to be measured flows during measuring, with the first light detector and the light source preferably being arranged at the two end faces of the measuring tube so that a measuring section is obtained which is as long as possible.

The second light detector (scattered light) is arranged in an advantageous manner substantially in the center between the light source and the first light detector on the side of the measuring chamber so that the scattered light can be captured at a small distance.

In order to be able to selectively supply the signals of the two light detectors to a display arrangement, the evaluation arrangement is preferably provided with a change-over device. This change-over device may be configured for manual change-over or be controlled automatically, with a control device being particularly suited in the latter case which supplies the measuring signals of the second light detector to the display arrangement below a predeterminable measuring signal level of the first light detector by changing over the change-over device. This ensures that, at low soot concentrations, the measurement takes place by way of the scattered light method which works with greater accuracy in this range.

Of course, it is also possible to use both measuring methods simultaneously, in which case the evaluation arrangement has two display arrangements for the signals of the two light detectors. This offers the possibility of a constant comparison between the two measuring methods.

For the implementation of correlation measurements, it is advisable to provide a comparator device for the signals of the two light detectors so that the comparison can be carried out automatically. By way of the comparator unit, a normalizing device for normalizing the signal of the one light detector as a function of the signal of the other light detector can be provided in an advantageous manner so that comparable measuring results are obtained.

BRIEF DESCRIPTION OF THE DRAWINGS

The single FIGURE shows a schematic representation of a measuring tube and a block diagram of an evaluation arrangement.

DESCRIPTION OF THE PREFERRED EMBODIMENTS.

A measuring tube 10 employed as a measuring chamber has a laterally disposed inlet 12 at one end region, which inlet is provided with a calibration valve 11, and a laterally disposed outlet 13 at the end region which lies opposite, which outlet is connected to a pump 14.

A light source 15 is arranged at the inlet-side end face of the measuring tube 10, and a first light detector 16, which normally is a photodetector, is arranged at the oppositely-disposed end face. An optical arrangement 17, shown schematically as a lens, concentrates the light beam, which is sent through the measuring tube 10 by the light source 15, on the first light detector 16. A light source-end optical arrangement 18, shown schematically as a reflector, serves to orient the light beam through the measuring tube 10. In the interest of simplification, optical elements which may be additionally required at the end faces of the measuring tube 10, if applicable, are not shown. The optical measuring section is limited in a known manner by measuring windows 8, 9. If the light source 15 is configured as a laser diode, optical arrangement can be eliminated to a large extent or altogether.

A second light detector 19 is arranged laterally on the outside of the measuring tube 10 between the light source 15 and the first light detector 16, with the second light detector capturing scattered light from a limited space region, with an optical arrangement 20, which is again shown schematically as a lens, supplying the scattered light generated in the measuring tube 10 by the light beam to the second light detector 19.

The measuring signals generated in the two light detectors 16, 19 are supplied to signal processing stages 21, 22, respectively, which may be configured, for example, as amplifiers or level matching stages. Furthermore, such signal processing stages may also comprise filters for locking out interfering signals or background noise. The output of the signal processing stage 21 can be connected via a change-over switch 23 with a measurement output unit such as a display or data acquisition arrangement 24 which, in the simplest case, may be configured as a digital or analog measuring instrument or as a screen display arrangement. The output of the other signal processing stage 22 is also connected with the change-over switch 23 via a normalizing unit 25 so that the processed signals of the two light detectors 16, 19 can be supplied selectively to the measurement output unit 24 by means of this change-over switch 23.

Furthermore, the output signals of the signal processing stages 21, 22 are supplied to a comparator unit 26 whose output signal acts upon the normalizing unit 25. In addition, the output signal of the signal processing stage 21 is supplied to a level control unit 27 by means of which the change-over switch 23 is placed into the shown switching position below a predeterminable signal level of the output signal of the signal processing stage 21, in which position the measurement output unit 24 receives the signals of the second light detector 19.

For the measurement, the fluid to be measured, for example, the exhaust gas of a motor vehicle, is guided through the measuring tube 10 in that the pump 14 works while the calibrating valve 11 is open. To this end, the exhaust pipe of a motor vehicle, not shown, for example, is connected with the calibrating valve 11 by a hose. For the zero balance, the calibrating valve 11 is changed over to the flushing position so that a flushing medium can be guided through the measuring chamber instead of the exhaust gas. Precipitates on the measuring windows can thus be detected and considered in the measuring result.

The light beam traveling through the measuring tube 10 from the light source 15 to the first light detector 16 is attenuated to a greater or lesser degree as a function of the soot constituents in the exhaust gas or of the turbidity of the fluid to be measured. The light attenuation during passage through absorbing media is evaluated according to the Lambert-Beer law. Via the change-over switch 23, the measuring signal evaluated in the signal processing stage 21 reaches the measurement output unit 24 where it indicates the degree of turbidity or the soot content in the exhaust gas. If the turbidity drops below a predeterminable level, the level control unit 27 responds and switches the change-over switch 23 into the switch position which is shown. In this manner, measuring signals of the second light detector 19 now reach the measurement output unit 24. The scattered light is captured by the second light detector 19, which scattered light is proportional to the concentration of the absorbing medium, i.e., for example, to the concentration of the soot in the exhaust gas. This measuring method is more accurate below a predeterminable turbidity than the opacimetric measuring method by way of the first light detector 16.

In order to obtain comparable measuring results, namely to make the transition between the different measuring methods a continuous one, the output signals of the two signal processing stages 21, 22 are supplied to a comparator unit 26 and control the normalizing unit 25 as a function of this comparison or of the respective deviation; the processed signals of the second light detector 19 are matched to those of the first light detector 16 by means of the normalizing unit. This may take place, for example, in that the respective measured curves are compared and matched with one another. In this manner, correlation measurements between the two methods can be carried out. Once limit values have been determined and set for the one system, these may thus be transferred to the other measuring method. By combining the comparator unit 26 with the normalizing unit 25, the respective measured values or measured curves can also be corrected. In individual cases, a normalizing unit may also be connected downstream of the signal processing stage 21 for this purpose.

By switching the change-over switch 23 back and forth, the measured values of the two methods can be displayed simultaneously on the measurement output unit 24. Of course, this may also take place in that both measuring lines are supplied to the measurement output unit 24 or to two separate display/data acquisition units without using a change-over switch 23.

The evaluation arrangement described may preferably be configured as a microprocessor.

I claim:

1. An arrangement for determining density and concentration of visible constituents in motor vehicle exhaust gas, comprising:

a light source (15);

a first light detector (16);

a measuring chamber (10) through which flows the exhaust gas, the light source (15) and the first light detector (16) being provided at two oppositely disposed points of the measuring chamber (10);

an evaluation means for evaluating a signal generated by the first light detector (16) as a first measure of the density and concentration; and a second light detector (19), disposed outside a radiation path through the measuring chamber (10) between the light source (15) and the first light detector (16), for capturing scattered light, wherein the evaluation means further comprises means for evaluating a signal generated by the second light detector (19) independently of the signal generated by the first light detector (16) as a second measure of the density and concentration, and normalizing means (25) for normalizing the signal of one of the first and second light detectors (16, 19) as a function of the signal of the other of the first and second light detectors (16, 19) so as to match the first and second measures of the density and concentration.

2. An arrangement according to claim 1, wherein the measuring chamber (10) is configured as a measuring tube through which the motor vehicle exhaust gas flows while the density and concentration of visible constituents therein are determined.

3. An arrangement according to claim 2, wherein the measuring tube (10) has two end faces, and wherein the first light detector (16) and the light source (15) are arranged at the two end faces of the measuring tube (10).

4. An arrangement according to claim 1, wherein the measuring chamber (10) has a side, and wherein the second light detector (19) is arranged substantially in the center between the light source (15) and the first light detector (16) on the side of the measuring chamber (10).

5. An arrangement claim 1, wherein the evaluation means further comprises a change-over unit (23) which selectively supplies the signals of the first and second light detector (16, 19) to a display or data acquisition arrangement.

6. An arrangement according to claim 5, wherein the evaluation means further comprises control unit means (27) for controlling the change-over device (23) so that the change-over device (23) supplies a measuring signal of the second light detector (19) to the display or data acquisition arrangement below a predeterminable measuring signal level of the first light detector (16) or of the second light detector (19).

7. An arrangement according to claim 5, wherein the change-over device (23) is configured such that it can be changed over manually.

8. An arrangement according claim 1, further comprising a measurement output unit (24) connected to the evaluation means, the measurement output unit (24) comprising display or data acquisition arrangements, or one display or data acquisition arrangement having two display options for the signals of the first and second light detectors (16, 19).

9. An arrangement according claim 1, wherein the evaluation means further comprises comparator means (26) for implementing correlation measurements for the signals of the first and second light detectors (16, 19).

10. An arrangement according to claim 9, wherein the normalizing means (25) is controlled by the comparator means (26).

11. An arrangement for measuring turbidity of a fluid, comprising;

a first light detector;

means for shining a beam of light on the first light detector, the beam of light passing through the fluid;

a second light detector which is disposed out of the beam of light and which receives light that has been scattered by the fluid;

a measurement output unit; and means for conveying a signal derived from the first light detector to the measurement output unit if the turbidity of the fluid is above a predetermined level and for conveying a signal derived from the second light detector to the measurement output unit if the turbidity of the fluid is below the predetermined level.

12. An arrangement according to claim 11, further comprising a measuring chamber having an inlet for the fluid and an outlet for the fluid, the beam of light passing through the measurement chamber.

13. An arrangement according to claim 12, wherein the fluid is exhaust gas from a motor vehicle, and further comprising a calibration valve for selectively conveying the exhaust gas or a calibration gas to the inlet of the measurement chamber.

14. An arrangement according to claim 11, wherein the means for conveying a signal comprises an electrically controlled switch, the electrically controlled switch being controlled by a control signal derived from one of the first and second light detectors.

15. An arrangement according to claim 11, wherein the means for conveying a signal comprises normalizing means for adjusting one of the signal derived from the first light detector and the signal derived from the second light detector so that they have a common signal level at the predetermined level of turbidity.

* * * * *